United States Patent [19]
Nugent

[11] Patent Number: 5,559,268
[45] Date of Patent: Sep. 24, 1996

[54] PROCESS FOR THE EFFICIENT PREPARATION OF N-SUBSTITUTED DEHYDROAMINO ACID ESTERS

[75] Inventor: William A. Nugent, Wilmington, Del.

[73] Assignee: E. I. Du Pont de Nemours and Company, Wilmington, Del.

[21] Appl. No.: 340,781

[22] Filed: Nov. 17, 1994

[51] Int. Cl.$^6$ .................................................. C07C 229/00
[52] U.S. Cl. ............................... 560/172; 554/112; 560/41
[58] Field of Search ...................... 560/172, 41; 554/112

[56] References Cited

U.S. PATENT DOCUMENTS

| | | | |
|---|---|---|---|
| 2,449,191 | 9/1948 | Behrens | 560/41 |
| 2,460,708 | 2/1949 | Mozingo | 560/172 |

OTHER PUBLICATIONS

M. Burk et al., Preparation and Use of $C_2$-Symmetric Bis(phospholanes): Production of α-Amino Acid Derivatives via Highly Enantioselective Hydrogenation Reactions, *J. Am. Chem. Soc.*, 115, 10125, (1993).

D. Schluter et al., Reactivity of N-acetyl-3-O-p-tolylsulfonyl-DL-serine methyl ester: nucleophilic displacement by water at C-3 versus elimination, *Carbohydrate Research*, 38, 333, (1974).

A. Srinivasen et al., Conversion of Threonine Derivatives to Dehydroamino Acids by Elimination of β–Chloro and O–Tosyl Derivatives, *J. Org. Chem.*, 42, 2256 (1977).

I. Photaki, Transformation of Serine to Cysteine. β–Elimination Reactions in Serine Derivatives, *J. Am. Chem. Soc.*, 85, 1123, (1963).

A. Brown et al., Symthesis of (±)-Versimide [Methyl α–(Methylsuccinimido)acrylate] and Related Compounds, *J. Chem. Soc., Perkin Trans.* 1, 65, (1972).

C. Balsamini et al., Stereospecific Synthesis of N–(Diphenylmethylene)–α–,β–didehydroamino Acid Methyl Esters from β–Hydroxy–α–amino Acids, *Synthesis*, 779, (1990).

R. Andruszieviwcz et al., Dehydration of β–Hydroxyamino Acids with N,N'–Carbonyldiimidazole, *Synthesis*, 968, (1982).

L. Somekh et al., Stereospecific Synthesis of α,β–Dehydroamino Acids from β–Hydroxy α–Amino Acid Derivatives, *J. Org. Chem.*, 48, 907, (1983).

*Primary Examiner*—Michael L. Shippen

[57] ABSTRACT

A process for the preparation of N-substituted dehydroamino acid esters by contacting a β-hydroxy-α-amino acid ester or N- or O-substituted β-hydroxy-α-amino acid ester with an excess of acetic anhydride and a base is disclosed.

8 Claims, No Drawings

PROCESS FOR THE EFFICIENT PREPARATION OF N-SUBSTITUTED DEHYDROAMINO ACID ESTERS

FIELD OF THE INVENTION

This invention relates to the preparation of N-substituted dehydroamino acid esters by dehydration of β-hydroxy-α-amino acid esters or N- or O-substituted β-hydroxy-α-amino acid esters.

BACKGROUND OF THE INVENTION

Dehydro α-amino acids are key intermediates for the manufacture of unnatural D-α-amino acids and non-proteinaceous α-amino acids using asymmetric hydrogenation technology. Such amino acids are increasingly important intermediates in the pharmaceutical, agrichemical, and flavor/fragrance industries. For example, the amino acid D-alanine is a component of an artificial sweetener alitame while non-proteinaceous 2-aminobutyric acid is a component of a tuberculostatic drug ethambutol. State-of-the-art asymmetric hydrogenation catalysts allow the manufacture of these α-amino acids with very high selectivity for a single enantiomer. For example, using rhodium catalysts bearing chiral phospholane ligands, the L- or D-isomer of alanine or 2-aminobutyric acid can be prepared from the corresponding dehydro amino acids in greater than 99% enantiomeric excess.

While aromatic dehydroamino acid derivatives such as dehydro phenylalanine are inexpensively available by the "Erlenmeyer synthesis", aliphatic analogous are more difficult to prepare. Of several methods devised to date, the most practical is the dehydration of the corresponding β-hydroxy-α-amino acid esters. Such routes avoid the use of expensive and hazardous reagents such as azides, t-butyl hypochlorite, pyruvic acid, or cysteine derivatives which are required in alternative routes. The approach is especially attractive in cases where the necessary β-hydroxy-α-amino acid is inexpensively available. Moreover, the hydroxyamino acid starting material need not be enantiomerically pure. For example, readily available DL-serine can be converted to dehydroalanine while threonine gives the precursor for 2-amino butyric acid.

Existing procedures for the dehydration of β-hydroxy-α-amino acids fall into two categories, namely stepwise processes and direct dehydration procedures. In the stepwise routes, the hydroxyl group is often first converted to a better leaving group, typically the p-toluenesulfonate. Alternatively, the hydroxyl group has been O-diphenylphosphorylated for this purpose. Both procedures utilize moisture-sensitive derivatizing agents. Another stepwise process involves activation of the amine functionality by converting it to a cyclic diamide, followed by dehydration using the acidic catalyst potassium bisulfate. A. G. Brown and T. C. Smale, *J. Chem. Soc., Perkin Trans. 1*, 65 (1972). All of these stepwise procedures are inherently inefficient since they involve the isolation and purification of a reactive intermediate.

Most of the direct dehydration processes utilize expensive reagents such as diisopropylcarbodiimide/copper(I) chloride, N,N'-carbonyldiimidazole, or DAST (diethylaminosulfur trifluoride). An alternative procedure uses moderately expensive diethyl chlorophosphate but additionally requires the hazardous (pyrophoric) base sodium hydride to effect elimination.

Thus there is a need for an improved single step dehydration process which uses reagents which are readily available, inexpensive and non-hazardous. The present invention provides such a process.

SUMMARY OF THE INVENTION

This invention provides a process for the preparation of N-substituted dehydroamino acid esters comprising contacting a β-hydroxy-α-amino acid ester or N- or O-substituted β-hydroxy-α-amino acid ester of formula I

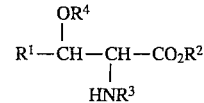

wherein $R^1$ is hydrogen, $C_1$–$C_{20}$ alkyl, a $C_3$ to $C_{20}$ cycloalkyl, a $C_6$–$C_{12}$ aryl, $C_7$ to $C_{20}$ aralkyl or $C_7$ to $C_{20}$ alkylaryl optionally substituted with $NR^5R^6$, $OR^5$, $(CO)OR^5$, $(CO)NR^5R^6$ or CN wherein $R^5$ and $R^6$ are each independently $C_1$–$C_6$ alkyl or $C_6$ aryl;

$R^2$ is $C_1$–$C_{20}$ alkyl, a $C_3$ to $C_{20}$ cycloalkyl, $C_6$–$C_{12}$ aryl, $C_7$ to $C_{20}$ aralkyl or $C_7$ to $C_{20}$ alkylaryl optionally substituted with $NR^5R^6$, $OR^5$, $(CO)OR^5$, $(CO)NR^5R^6$ or CN wherein $R^5$ and $R^6$ are each independently $C_1$–$C_6$ alkyl or $C_6$ aryl;

$R^3$ is hydrogen, $C_1$–$C_{20}$ acyl, $C_1$–$C_{20}$ alkyl, a $C_3$ to $C_{20}$ cycloalkyl, a $C_6$–$C_{12}$ aryl, a $C_7$ to $C_{20}$ aralkyl or a $C_7$ to $C_{20}$ alkylaryl optionally substituted with $NR^5R^6$, $OR^5$, $(CO)OR^5$, $(CO)NR^5R^6$ or CN wherein $R^5$ and $R^6$ are each independently $C_1$–$C_6$ alkyl or a $C_6$ aryl;

$R^4$ is H or $C_1$–$C_{20}$ acyl; with an excess of acetic anhydride and a base to yield an N-substituted dehydroamino acid ester of formula II

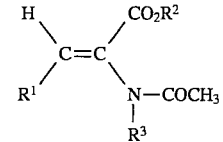

wherein $R^1$, $R^2$ and $R^3$ are as defined above in formula I

DETAILED DESCRIPTION OF THE INVENTION

This invention provides a process for the preparation of N-substituted dehydroamino aged esters.

The term "acyl" as used herein denotes

wherein R is hydrogen $C_1$–$C_{20}$ alkyl, $C_6$–$C_{14}$ aryl, $C_7$–$C_{20}$ aralkyl, $C_7$–$C_{20}$ alkylaryl and their various isomers.

The term "alkyl" as used herein denotes a straight-chain or branched-chain alkyl such as methyl, ethyl, n-propyl, i-propyl, or the different butyl, pentyl, hexyl, and other isomers up to 20 carbon atoms.

The term "cycloalkyl" denotes a cyclic alkyl such as cyclopropyl, cyclobutyl, cyclopentyl, cyclohexyl, and others up to 20 carbon atoms.

The term "aryl" denotes aromatic groups such as phenyl, 1-naphthyl, 2-naphthyl, or biphenylyl.

The term "aralkyl" denotes aromatic groups having at least one alkyl substituent linked via a carbon atom of the aromatic group. Examples include benzyl, α-phenethyl and β-phenethyl.

The term "alkylaryl" denotes aromatic groups having at least one alkyl substituent linked via a carbon atom of the alkyl substituent. Examples include o-tolyl, m-tolyl, p-tolyl, and p-t-butylphenyl.

The process of the present invention for preparation of esters of N-substituted dehydroamino acid esters by contacting an β-hydroxy-α-amino acid ester or an N- or O-substituted β-hydroxy-α-amino acid ester with acetic anhydride and a base is shown in equation 1) below:

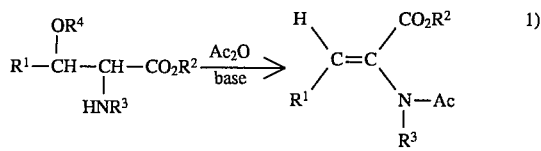

wherein
$R^1$, $R^2$, $R^3$, and $R^4$ are as defined above in formula I.

Examples include the preparation of methyl α-(N,N-diacetyl)amido acrylate (obtained as a mixture with the monoacetamide) from serine methyl ester shown in equation 2) below and the preparation of methyl α-(N,N-diacetyl)amido-Z-crotonate from threonine methyl ester, as shown in equation 3) below:

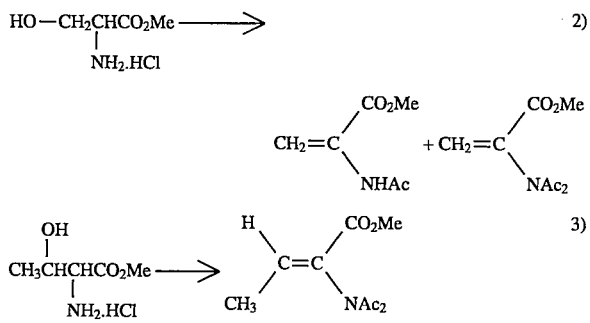

Bases suitable for use in the process of the present invention are inorganic or organic. The conjugate acid of said base has a $pK_a$ in the range of about 4.75 to about 14, preferably 4.75 to about 10, most preferably 4.75 to 8. Examples of suitable inorganic bases include various ester salts such as sodium acetate, potassium acetate, sodium carbonate, potassium carbonate, sodium bicarbonate, potassium bicarbonate. Examples of suitable organic bases for the process of the present invention include tertiary amine bases. Examples include pyridine, picoline, diisopropylethylamine, triethylamine, tributylamine, N-methyl morpholine, DABCO (1,4-diazabicyclo [2.2.2]-octane), and DBU (1,8-diazabicyclo [5.4.0] undec-7-ene). The molar ratio of base to reactant is from about 1:1 to about 30:1. Preferably the molar ratio of base to reactant is from about 1:1 to about 15:1. A range of 3:1 to 7:1 is most preferred.

The β-hydroxy-α-amino acid ester or N- or O-substituted β-hydroxy-α-amino acid ester starting materials of the process may be utilized as a free base or may be introduced as a salt such as a hydrochloride, sulfate, or oxalate salt. Many such compounds are available commercially or may be prepared by methods known in the art, as further demonstrated by Example 7 herein.

The process of the invention can be carried out at atmospheric pressure or at pressures between 100 and 1000 $kP_a$. Reaction at atmospheric pressure is preferred. The process is preferably carried out under air, but an inert atmosphere such as nitrogen or argon may be utilized.

The preferred solvent is excess acetic anhydride. However, organic co-solvents may optionally be used; examples of suitable organic co-solvents include toluene, xylene, chlorobenzene, pyridine, di-n-butyl ether, and dimethyl acetamide.

The reaction is carried out over a temperature range of from about 80° C. to about 200° C. Preferably, the reaction is conducted at a temperature of from about 100° C. to 180° C. A range of 120° C. to 150° C. is most preferred. Reaction times can vary from about 0.5 hour to about 48 hours. A time of 1 to 4 hours is preferred.

Agitation during the reaction is preferable since it is conducted under reflux conditions. The product is isolated using conventional techniques such as distillation, extraction, or chromatography. The product is obtained as a mono- or di-N-acetyl derivative, or a mixture thereof.

The current invention provides advantages over prior art processes in several respects. The reagents used for dehydration, preferably acetic anhydride and a base such as sodium acetate or pyridine, are cheap and relatively innocuous. No separate step is required either to protect the amine functionality or to activate the hydroxyl group toward elimination. The product dehydro-α-amino acid is obtained as a mono- or di-N-acetyl derivative; the acetyl group is a suitable directing group for subsequent asymmetric hydrogenation.

The process of the present invention is useful for the preparation of dehydroamino esters. Such esters are useful starting materials in asymmetric hydrogenation reactions to prepare particular isomers of α-amino acids of importance in the pharmaceutical, agrichemical, and flavor/fragrance industries.

The following Examples demonstrate the process of the invention. The amino acid starting materials used in these examples are commercially available from Sigma Chemical Company, St. Louis, Mo.

EXAMPLE 1

A mixture of DL-serine methyl ester hydrochloride (15.6 g, 100 mmol), pyridine (50 mL), and acetic anhydride (100 mL) was heated at reflux for 2 hours. Excess solvent was removed at reduced pressure. The residue was added to water (250 mL) and was extracted into ether (500 mL). The ether phase was stirred 1 hour with saturated aqueous sodium bicarbonate (100 mL), washed with water (50 mL), and dried with magnesium sulfate. Removal of ether at reduced pressure afforded 8.40 g of an amber oil which was shown to be a mixture of methyl α-acetamido acrylate and methyl α-(N,N-diacetyl)amido acrylate by NMR spectroscopy. A portion of this product was vacuum distilled to afford material (3.01 g) boiling at 63°–72° C. at 0.5 torr (66.7 pa) which was enriched in methyl α-acetamido acrylate and a fraction (2.28 g) boiling at 72°–74° C. which was shown to be substantially pure methyl α-(N,N-diacetyl)amido acrylate by $^1H$ and $^{13}C$ NMR. For the diamide $^1H$ NMR (CDCl$_3$/TMS): σ2.36 (s, 6H), 3.83 (s, 3H), 5.82 (s, 1H), 6.60 (s, 1H); $^{13}C$ NMR (CDCl$_3$/TMS): σ25.97, 52.90, 128.00, 137.16, 163.30, 172.10. For the monoamide $^1H$ NMR (CDCl$_3$/TMS): σ2.15 (s, 3H), 3.84 (s, 3H), 5.90 (s, 1H), 6.60 (s, 1H), 7.81 (broad s, 1H); $^{13}C$ NMR (CDCl$_3$/TMS): σ24.66, 52.96, 108.66, 130.82, 164.55, 168.77.

EXAMPLE 2

A mixture of L-threonine methyl ester hydrochloride (17.0 g, 100 mmol), pyridine (50 mL), and acetic anhydride (100 mL) was heated at reflux for 2 hours. Excess solvent was removed at reduced pressure. The residue was added to water (250 mL) and was extracted into ether (500 mL). The ether phase was stirred 1 hour with saturated aqueous sodium bicarbonate (100 mL), washed with water (50 mL), and dried with magnesium sulfate. Removal of ether at reduced pressure afforded a residue which was distilled (76°–82° C. at 0.25 torr (33.3 pa) ) to afford methyl α-(N,N-diacetyl) amido-Z-crotonate (11.95 g, 60%) as a pale yellow oil. $^1$H NMR (CDCl$_3$/TMS): σ1.80 (d, J=7, 3H), 2.32 (s, 6H), 3.80 (s, 3H), 7.22 (q, J=7, 1H); $^{13}$C NMR (CDCl$_3$/TMS): σ13.37, 25.44, 52.35, 130.66, 140.36, 163.52, 171.73.

EXAMPLE 3

A round-bottomed flask was charged with L-threonine methyl ester hydrochloride (17.0 g, 0.10 mol), anhydrous sodium acetate (50 g, 0.61 mol), and acetic anhydride (150 mL). After heating at reflux for 2 hours, volatiles were removed at reduced pressure. The residue was taken up in ether (250 mL) and was washed twice with water (250 mL, 50 mL). Volatiles were removed at reduced pressure and the residue was distilled at 86°–90° C. at 0.4 torr (53.3 pa) to give α-(N,N-diacetyl)-amido-Z-crotonate (13.82 g, 69%) as a pale yellow liquid. $^1$H NMR (CDCl$_3$/TMS): σ1.80 (d, J=7, 3H), 2.32 (s, 6H), 3.80 (s, 3H), 7.22 (q, J=7, 1H); $^{13}$C NMR (CDCl$_3$/TMS): σ13.37, 25.44, 52.35, 130.66, 140.36, 163.52, 171.73.

EXAMPLE 4

A mixture of crushed anhydrous potassium carbonate (5.0 g, 35 mmol), L-threonine methyl ester hydrochloride (1.70 g, 10 mmol), and acetic anhydride (15 mL) was heated at reflux for 2 hours. Upon cooling the resultant solid mass was stirred with ether (25 mL) and water (25 mL). The ether layer was washed with additional water (5 mL) and volatiles were distilled off at reduced pressure to afford 1.17 g of a red oil. This crude residue was shown by NMR spectroscopy to contain, in addition to some unreacted acetic anhydride, α-(N,N-diacetyl)amido-Z-crotonate as the principal component. $^1$H NMR (CDCl$_3$/TMS): σ1.80 (d, J=7, 3H), 2.32 (s, 6H), 3.80 (s, 3H), 7.22 (q, J=7, 1H); $^{13}$C NMR (CDCl$_3$/TMS): σ13.37, 25.44, 52.35, 130.66, 140.36, 163.52, 171.73.

EXAMPLE 5

A mixture of sodium bicarbonate (5.0 g, 60 mmol), DL-serine methyl ester hydrochloride (1.56 g, 10 mmol), and acetic anhydride (15 mL) was heated at reflux for 2 hours. Upon cooling the resultant mixture was stirred with ether (25 mL) and water (25 mL). The ether layer was washed with additional water (5 mL) and volatiles were distilled off at reduced pressure to afford 1.17 g of an amber liquid. A few crystals of hydroquinone were added to inhibit polymerization. The crude residue was shown by NMR spectroscopy to contain, in addition to some unreacted acetic anhydride, a mixture of methyl α-acetamido acrylate and methyl α-(N,N-diacetyl)amido acrylate in a roughly 2:3 molar ratio. For the diamide $^1$H NMR (CDCl$_3$/TMS): σ2.36 (s, 6H), 3.83 (s, 3H), 5.82 (s, 1H), 6.60 (s, 1H); $^{13}$C NMR (CDCl$_3$/TMS): σ25.97, 52.90, 128.00, 137.16, 163.30, 172.10. For the monoamide $^1$H NMR (CDCl$_3$/TMS): σ2.15 (s, 3H), 3.84 (s, 3H), 5.90 (s, 1H), 6.60 (s, 1H), 7.81 (broad s, 1H); $^{13}$C NMR (CDCl$_3$/TMS): σ24.66, 52.96, 108.66, 130.82, 164.55, 168.77.

EXAMPLE 6

A mixture of serine benzyl ester hydrochloride (4.63 g, 20 mmol), sodium acetate (10 g, 12 mmol), and acetic anhydride (30 mmol) was heated at reflux for 2 hours. Volatiles were removed at reduced pressure and the residue was taken up in ether and washed (50 mL each). The ether layer was washed with additional water (10 mL) and the volatiles were removed at reduced pressure to afford 5.83 g of crude product as an amber liquid. The residue was purified by flash chromatography on silica using 3:1 hexane/ethyl acetate as solvent. The product obtained in this way (4.44 g, 88%) was a 3:1 mixture of benzyl α-acetamido acrylate and benzyl α-(N,N-diacetyl)amino acrylate and its identity was confirmed by $^1$H and $^{13}$C NMR spectroscopy. For the diamide $^1$H NMR (CDCl$_3$/TMS): σ2.33 (s, 6H), 5.25 (s, 2H), 5.82 (s, 1H), 6.62 (s, 1H), 7.3–7.4 (m, 5H). For the monoamide $^1$H NMR (CDCl$_3$/TMS): σ2.11 (s, 3H), 5.26 (s, 2H), 5.94 (s, 1H), 6.60 (s, 1H), 7.3–7.4 (m, 5H), 7.76 (broad s, 1H). For the mixture of diamide and monoamide $^{13}$C NMR. (CDCl$_3$/TMS): σ24.58, 25.93, 67.64, 67.72, 108.90, 128.04, 128.12, 128.20, 128.46, 128.53, 128.60, 130.91, 135.02, 135.05, 137.19, 162.65, 163.92, 168.82, 172.08.

EXAMPLE 7

A mixture of N,O-diacetyl DL-threonine methyl ester (2.07 g, 9.5 mmol), pyridine (5 mL), and acetic anhydride (10 mL) was heated at reflux for 2 hours. Volatiles were distilled off at reduced pressure and the residue was taken up in ether (50 mL). The ether solution was washed twice with water (25 mL) and the volatiles were removed at reduced pressure. The resultant red oil was shown by NMR spectroscopy to contain, in addition to some unreacted acetic anhydride, α-(N,N-diacetyl) amido-Z-crotonate as the principal component. $^1$H NMR (CDCl$_3$/TMS): σ1.80 (d, J=7, 3H), 2.32 (s, 6H), 3.80 (s, 3H), 7.22 (q, J=7, 1H); $^{13}$C NMR (CDCl$_3$/TMS): σ13.37, 25.44, 52.35, 130.66, 140.36, 163.52, 171.73.

The N,O-diacetyl DL-threonine methyl ester employed as a starting material in this example was prepared as follows: A mixture of threonine methyl ester hydrochloride (5 g), pyridine (15 mL), and acetic anhydride (15 mL) was stirred at room temperature overnight. Volatiles were removed at reduced pressure and the residue was added to ether (200 mL). The resultant ether solution was decanted away from the solid precipitate and the solvent was distilled at reduced pressure to give crude product which was crystallized from toluene to give the desired product (2.26 g) as a white crystalline solid, mp 112° C. $^1$H NMR (CDCl$_3$/TMS): σ1.27 (d, J=7, 3H), 2.03 (s, 3H), 2.10 (s, 3H), 3.73 (s, 3H), 4.80 (dd, J=3, 12, 1H), 5.43 (dq, J=3, 7, 1H), 6.17 (broad d, J=12, 1H); $^{13}$C NMR (CDCl$_3$/TMS): σ17.30, 21.09, 23.32, 52.90, 55.56, 70.60, 169.85, 170.50, 170.60.

EXAMPLE 8

A mixture of DL-serine methyl ester hydrochloride (15.6 g, 0.1 mol), diisopropylethylamine (50 mL), and acetic anhydride (100 mL) were heated at reflux for 2 hours. The volatiles were distilled off at high vacuum and the residue was taken up in ether (500 mL) and washed with 1N HCl (100 mL). Saturated aqueous sodium bicarbonate (100 mL) was added and the mixture was stirred 1 hour. The ether layer was washed with water (50 mL) and was dried over magnesium sulfate. The solvent was removed at reduced pressure and the red liquid residue was distilled to afford a fraction (4.00 g) boiling at 60°–65° C. at 0.5 torr (66.7 pa)

which was enriched in methyl α-acetamido acrylate and a fraction (5.57 g) boiling at 87°–97° C. at 1.2 torr (160 pa) which was shown to be substantially pure methyl α-(N,N)-diacetyl)amido acrylate by $^1$H and $^{13}$C NMR. For the diamide $^1$H NMR (CDCl$_3$/TMS): σ2.36 (s, 6H), 3.83 (s, 3H), 5.82 (s, 1H), 6.60 (s, 1H); $^{13}$C NMR (CDCl$_3$/TMS): σ25.97, 52.90, 128.00, 137.16, 163.30, 172.10. For the monoamide $^1$H NMR (CDCl$_3$/TMS): σ2.15 (s, 3H), 3.84 (s, 3H), 5.90 (s, 1H), 6.60 (s, 1H), 7.81 (broad s, 1H); $^{13}$C NMR (CDCl$_3$/TMS): σ24.66, 52.96, 108.66, 130.82, 164.55, 168.77.

What is claimed is:

1. A process for the preparation of N-substituted dehydroamino acid esters comprising contacting a β-hydroxy-α-amino acid ester or N- or O-substituted β-hydroxy-α-amino acid ester of formula I

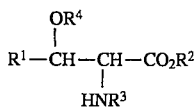

wherein

R$^1$ is hydrogen, C$_1$–C$_{20}$ alkyl, a C$_3$ to C$_{20}$ cycloalkyl, a C$_6$–C$_{12}$ aryl, C$_7$ to C$_{20}$ aralkyl or C$_7$ to C$_{20}$ alkylaryl optionally substituted with NR$^5$R$^6$, OR$^5$,(CO)OR$^5$, (CO)NR$^5$R$^6$ or CN wherein R$^5$ and R$^6$ are each independently C$_1$–C$_6$ alkyl or C$_6$ aryl;

R$^2$ is C$_1$–C$_{20}$ alkyl, a C$_3$ to C$_{20}$ cycloalkyl, C$_6$–C$_{12}$ aryl, C$_7$ to C$_{20}$ aralkyl or C$_7$ to C$_{20}$ alkylaryl optionally substituted with NR$^5$R$^6$, OR$^5$, (CO)OR$^5$, (CO)NR$^5$R$^6$ or CN wherein R$^5$ and R$^6$ are each independently C$_1$–C$_6$ alkyl or C$_6$ aryl;

R$^3$ is hydrogen, C$_1$–C$_{20}$ acyl, C$_1$–C$_{20}$ alkyl, a C$_3$ to C$_{20}$ cycloalkyl, a C$_6$–C$_{12}$ aryl, a C$_7$ to C$_{20}$ aralkyl or a C$_7$ to C$_{20}$ alkylaryl optionally substituted with NR$^5$R$^6$, OR$^5$, (CO)OR$^5$, (CO)NR$^5$R$^6$ or CN wherein R$^5$ and R$^6$ are each independently C$_1$–C$_6$ alkyl or a C$_6$ aryl;

R$^4$ is H or C$_1$–C$_{20}$ acyl;

with an excess of acetic anhydride and a base to yield an N-substituted dehydroamino acid ester of formula II

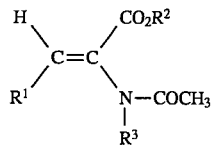

wherein R$^1$, R$^2$ and R$^3$ are as defined above in formula I.

2. The process of claim 1 further comprising a cosolvent selected from the group consisting of toluene, xylene, chlorobenzene, pyridine, di-n-butyl ether or dimethyl acetamide.

3. The process of claim 1 wherein the base is an inorganic or organic base the conjugate acid of which has a pK$_a$ of from about 4.75 to about 14.

4. The process of claim 3 wherein the base is selected from the group consisting of sodium acetate, potassium acetate, sodium carbonate, potassium carbonate, sodium bicarbonate, potassium bicarbonate, pyridine, picoline, diisopropylethylamine, triethylamine, tributylamine, N-methyl morpholine, 1,4-diazabicyclo[2,2,2]octane, and 1,8-diazabicyclo[5,4,0]undec7-ene.

5. The process of claim 3 wherein the molar ratio of base to reactant is from about 1:1 to about 30:1.

6. The process of claim 5 wherein the molar ratio of base to reactant is from about 3:1 to about 7:1.

7. The process of claim 1 conducted at a temperature of from about 80° C. to about 200° C.

8. A process for the preparation of N-substituted dehydroamino acid esters comprising contacting a β-hydroxy-α-amino acid ester or N- or O-substituted β-hydroxy-α-amino acid ester of formula I

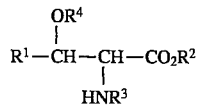

wherein

R$^1$ is hydrogen, C$_1$–C$_{20}$ alkyl, a C$_3$ to C$_{20}$ cycloalkyl, a C$_6$ aryl, C$_7$ to C$_{20}$ aralkyl or C$_7$ to C$_{20}$ alkylaryl optionally substituted with NR$^5$R$^6$, OR$^5$,(CO)OR$^5$, (CO)NR$^5$R$^6$ or CN wherein R$^5$ and R$^6$ are each independently C$_1$–C$_6$ alkyl or C$_6$ aryl;

R$^2$ is C$_1$–C$_{20}$ alkyl, a C$_3$ to C$_{20}$ cycloalkyl, C$_6$ aryl, C$_7$ to C$_{20}$ aralkyl or C$_7$ to C$_{20}$ alkylaryl optionally substituted with NR$^5$R$^6$, OR$^5$, (CO)OR$^5$,(CO)NR$^5$R$^6$ or CN wherein R$^5$ and R$^6$ are each independently C$_1$–C$_6$ alkyl or C$_6$ aryl;

R$^3$ is hydrogen, C$_1$–C$_{20}$ acyl, C$_1$–C$_{20}$ alkyl, a C$_3$ to C$_{20}$ cycloalkyl, a C$_6$ aryl, a C$_7$ to C$_{20}$ aralkyl or a C$_7$ to C$_{20}$ alkylaryl optionally substituted with NR$^5$R$^6$, OR$^5$, (CO)OR$^5$,(CO)NR$^5$R$^6$ or CN wherein R$^5$ and R$^6$ are each independently C$_1$–C$_6$ alkyl or a C$_6$ aryl;

R$^4$ is H or C$_1$–C$_{20}$ acyl;

with an excess of acetic anhydride and a base to yield an N-substituted dehydroamino acid ester selected from the group consisting of methyl α-(N,N-diacetyl)amido acrylate and methyl α-(N,N-diacetyl)amido-Z-crotonate.

* * * * *